(12) United States Patent
Russell

(10) Patent No.: US 9,585,898 B2
(45) Date of Patent: Mar. 7, 2017

(54) METHOD FOR THE REDUCTION OF DANGEROUS BLOOD SUGAR LEVELS

(76) Inventor: Kenneth O. Russell, Houston, TX (US)

(*) Notice: Subject to any disclaimer, the term of this patent is extended or adjusted under 35 U.S.C. 154(b) by 0 days.

(21) Appl. No.: 12/069,505

(22) Filed: Feb. 11, 2008

(65) Prior Publication Data

US 2009/0203656 A1   Aug. 13, 2009

(51) Int. Cl.
| | |
|---|---|
| *A61K 31/60* | (2006.01) |
| *A61K 31/555* | (2006.01) |
| *A61K 31/44* | (2006.01) |
| *A61K 31/616* | (2006.01) |
| *A61K 9/00* | (2006.01) |
| *A61K 31/198* | (2006.01) |
| *A61K 31/28* | (2006.01) |
| *A61K 31/455* | (2006.01) |
| *A61K 33/24* | (2006.01) |
| *A61K 45/06* | (2006.01) |

(52) U.S. Cl.
CPC ............ *A61K 31/616* (2013.01); *A61K 9/006* (2013.01); *A61K 31/198* (2013.01); *A61K 31/28* (2013.01); *A61K 31/455* (2013.01); *A61K 33/24* (2013.01); *A61K 45/06* (2013.01); *A61K 31/555* (2013.01)

(58) Field of Classification Search
CPC ... A61K 31/616; A61K 31/555; A61K 31/455
USPC ......................................... 514/165, 184, 356
See application file for complete search history.

(56) References Cited

U.S. PATENT DOCUMENTS

| | | | |
|---|---|---|---|
| 4,571,391 A | 2/1986 | Riley et al. | |
| 4,923,855 A | 5/1990 | Jensen | |
| 5,087,623 A | 2/1992 | Boynton et al. | |
| 5,087,624 A | 2/1992 | Boynton et al. | |
| 5,567,736 A | 10/1996 | Buchman et al. | |
| 5,905,075 A | 5/1999 | Harpe et al. | |
| 5,948,772 A | 9/1999 | de la Harpe et al. | |
| 5,962,030 A * | 10/1999 | Fine .............................. | 424/646 |
| 5,980,905 A | 11/1999 | de la Harpe et al. | |
| 6,093,711 A | 7/2000 | de la Harpe et al. | |
| 6,100,250 A | 8/2000 | de la Harpe et al. | |
| 6,100,251 A | 8/2000 | de la Harpe et al. | |
| 6,136,317 A | 10/2000 | de la Harpe et al. | |
| 6,143,301 A | 11/2000 | de la Harpe et al. | |
| 6,147,070 A | 11/2000 | Facchini | |
| 6,203,819 B1 | 3/2001 | Fine | |
| 6,251,888 B1 | 6/2001 | de la Harpe et al. | |
| 6,251,889 B1 | 6/2001 | de la Harpe et al. | |
| 6,258,848 B1 | 7/2001 | Fantus | |

OTHER PUBLICATIONS

Silveira et al., "Comparative effects of physical training and metformin in diabetic rats", Open Clinical Chemistry Journal, vol. 1, pp. 13-16 (2008).*
Sargent T, Lim TH, Jenson, RL:"Reduced CHromium Retention in Patients with Hemochromatosis, a Possible Basis of Hemechromatotic Diabetes." Metabolism: 1979: 28:1, p. 70-79.
Maher, Timothy J. Chromium and Other Minerals in Diabetes Mellitus, U.S. Pharmacist, 2000: 24: 11.
Vincent, 1., Biochemistry ofChromiwn, 1. Nutrition 2000;130:715-718.
vBrock, 1.H., "Transferrins." Harrison P. (ed) Metalloproteins 1985: vol. 2: 183-262 MacMillan, London.
Lim, T. Sargent, T., Kusubov, N. "Kinetics of Trace Element Chromium (iII) in the Human Body" Am 1. P'hysiology, 1983: 244(4): R445-54.
Davies, S., et al, "Age-related decreases in chromium levels in 51,665 hair, sweat, and serum samples from 20,872 patients implications for the prevention of cardiovascular disease and Type II diabetes mellitus", Metabolism, 1997; 46(5) 469-473.
Jiang, G., Zhang, B."Glucagon and Regulation of Glucose Metabolism" Am JPhsiol Endocrinol Metab. 2003 284: E671-8.
Jeejeehboy, K., et ai, "Chromium Deficiency, Glucose Intolerance and Neuropathy reversed by Chromium Supplementation ina Patient Receiving Long-Term Parenteral Nutrition:".

* cited by examiner

*Primary Examiner* — Kevin E Weddington
(74) *Attorney, Agent, or Firm* — Pham IP Group; Frank H. Pham

(57) ABSTRACT

The present invention relates to a method and procedure for reducing immediate serum glucose levels without resort to drugs. Specifically, the invention discloses a regular regimen comprising modest exercise, daily nutritional supplements and a series of specific, time sensitive steps, which, when followed will optimize the effects of the invention.

9 Claims, No Drawings

METHOD FOR THE REDUCTION OF DANGEROUS BLOOD SUGAR LEVELS

REFERENCE TO PROVISIONAL PATENT FILLING

On Feb. 10, 2007, the Inventor filed a provisional patent disclosure entitled Method for the Long-Term Reduction of Dangerous Blood Sugar Levels from which this application is derived.

CIRCUMSTANCES OF CONCEPTION

The Inventor suffers from iron overloading. This is a common result of the contemporary American diet which includes too much fructose and vitamin c (both of which cause too much iron to be absorbed). The extra iron builds up in organs and damages them. Without treatment, the disease can cause these organs to fail.

Healthy people usually absorb about 10 percent of the iron contained in the food they eat to meet the body needs. People with a genetic inclination to absorb excess iron suffer from hemochromatosis and frequently become diabetic. Their body has no natural way to rid itself of the excess iron, so it is stored in body tissues, especially the liver, heart, and pancreas.

Excess iron depletes the body's ability to process chromium[i]. Chromium is a necessary co-factor with insulin, in the normal digestion of glucose and other sugars[ii]. Without chromium to assist the insulin, the metabolism is only one-sixth as effective in processing glucose[iii] and the sufferer is deemed to have Type II Diabetes Mellitus, the complications of which (heart disease, hypertension, liver cancer, kidney failure, strokes, etc.) are the largest causes of early death worldwide.

Upon being diagnosed as Diabetic, the Inventor had to make a choice to either quietly accept his fate along with millions of other Diabetics or fight it. He chose to learn all he could of the disease and search for a cure. Common medical wisdom says that Diabetes is incurable and sufferers can only hope to mitigate the symptoms and must accept a significantly degraded quality of life. The Inventor found otherwise.

Mechanism of Sugar Metabolism

Soon after the introduction of sugars into the blood stream, the pancreas begins production of insulin. The insulin, when injected into the blood stream, unites with a co-factor, a chromium-binding oligopeptide produced in the liver, called Glucose Tolerance Factor[iv] (GTF), or, sometimes, Low Molecular Weight Chromium factor (LMWCr). This oligopeptide normally contains an ion of Chromium in the plus 3 oxidation state (Cr+3) and is part of an auto-amplification mechanism for insulin signaling.

The insulin with its GTF co-factor has been shown to activate the tyrosine kinase activity of the insulin receptor of cells in response to insulin. This allows the Cr3+ to move from the blood into the cells of the insulin-sensitive tissues, which amplifies the importation of glucose into the cells. The oligopeptide then becomes inactive and as Chromodulin, is filtered by the kidneys for elimination in the urine. If there is insufficient Chromium in the Liver, the oligopeptide still is produced but is one sixth as effective in catalyzing the insulin process as it is with the Cr+3 ion present.

Chromium normally enters the body as a trace element in food. Free Chromium, however, cannot exist in the blood stream due to the chelating effect of the sugars present therein. Free Chromium is immediately, and almost entirely complexed out by blood glucose as the chelate Chromium Gluconate, which is eliminated in the urine.

To survive transit from the intestines to the liver, where the GTF is produced, Cr+3 in the intestines is loaded onto a molecule known as Transferrin, a plasma protein which transports both Iron and Chromium to the liver. In healthy persons, the Transferrin ratio of Chromium to Iron is 7:3[v], however, if there is insufficient Chromium in the diet, or if there is excess Iron in the system, this ratio changes dramatically. In Hemochromatosis victims, the Transferrin molecules are almost entirely loaded with Iron.

Chromium, offloaded from the Transferrin, is stored in the Liver, kidneys, bone marrow and other soft tissues[vi]. The most significant source of chromium, therefore for humans has previously been organ meats such as liver and kidneys. These food sources are no longer consumed in significant amounts, and thus the chromium contained therein is not available. In modern diets, this optimal 7:3 mix is usually out of balance because of two factors. First, the highly refined foods in the modern diet remove most of the naturally present chromium in the processing. Second, the overabundance of dietary carbohydrates loads the gut with glucose, which readily forms Chromium Gluconate, thus eliminating most of the free chromium which is present in the gut prior to its reaching the transferrin.

With each cycle of the iron and chromium loaded transferrin between the intestinal walls and the liver, the ratio of iron to chromium contained in the transferrin tends to change. If the metal ion transport ratio of the transferrin reaches 60% iron and 40% chromium, the liver must deal with twice the optimal iron load and slightly more than half of the required amount of chromium.

This prevailing tendency, of accumulating excess iron at the expense of chromium, is implicated as one of the potential causes for not only diabetes mellitus, but also heart disease, high lipids, hyper tension, cirrhosis of the liver, gout, macular degeneration and glaucoma.

The highest levels of chromium are present at the time of birth. Several large population studies indicate that chromium in the tissues of carbohydrate overloaded humans declines continuously throughout the course of life[vii]. The normal daily demand for production of GTF will eventually deplete the liver's store of Cr+3 if not replenished through the diet. Once the liver is unable to provide a Cr+3 ion for every GTF produced, the normal sugar metabolism becomes inefficient and Diabetes Milletis ensues.

The Insulin Resistance Paradigm:

Insulin resistance is the phrase given to the phenomenon of a person's maintaining higher than normal blood sugar levels even though the pancreas is producing a normal amount of insulin. Insulin resistance is almost always associated with an excess of fat stored in the liver, which is called "Fatty Liver" syndrome.

Glucose is a necessary component in normal metabolism, but in diabetics, this metabolism gets out of balance. When cells are in need of glucose, there is an enzymatic signal sent to the pancreatic alpha cells which respond by releasing glucagon, which in turn triggers the release, by the liver, of more glucose into the blood[viii]. However, the presence of this blood glucose stimulates the pancreatic beta cells to create insulin and inject it into the blood stream. But when the GTF is missing the necessary chromium ion, the insulin is only one-sixth as effective in transporting the available glucose into the cells. The glucose-starved cells continue to emit the enzymatic signal to produce more glucose, completing the cyclic dysfunction. Thus, the pancreas is simultaneously producing both Glucagon, to trigger glucose delivery to the cells and Insulin, to metabolize the extra glucose.

Consuming excess carbohydrates at meals does nothing to correct the shortage of glucose transport into the cells. The metabolic process has been impaired by an endemic shortage of chromium, and dramatically reduced insulin effectiveness. This suggests that the (fatty) liver can maintain high blood glucose levels for an extended period of time.

Diabetics achieve only limited satiation from food they ingest because the abundance of glucose in their systems is not drawn into the cells that need the glucose. The diabetic normally has an adequate supply of fat which the liver can readily convert to glucose. Obesity frequently results, as the unsatisfying meals leave the victim continuously hungry and therefore still eating. In addition, un-metabolized glucose is ultimately converted by the liver to further fat for storage. Fatigue is also a common result of the intracellular glucose shortage as the muscle cells are denied adequate amounts of energy (glucose).

In summary, newly diabetic persons usually have sufficient insulin to adequately handle the daily glucose needs of the cells, however, the chromium-depleted GTF is unable to facilitate the efficient transport of glucose across the cell walls. This has the effect of building the serum glucose to dangerous levels and has the dual, undesirable result of overworking and thus wearing out the pancreas while at the same time subjecting tissues to toxic levels of glucose. After prolonged absence of Cr+3, the pancreas beta cells become over-worked and eventually are unable to produce sufficient Insulin.

The most common form of adult onset diabetes, therefore, is the result of the body's supplies of available chromium being depleted, which leads to a deficiency of chromium at the liver during the synthesis of GTF. Generally, women have higher chromium levels than men[ix], however, during pregnancy, woman must provide the high levels of chromium demanded by the developing fetus, which depletes her natural stores. Pregnant women thus often develop Gestational Diabetes, brought on by the forced chromium shortage. This condition is usually reversible after birth providing the woman can replenish the chromium stores in her body's storage locations. Patients on prolonged intravenous feeding can develop Diabetes simply due to the absence of Cr+3 in the drip. This condition is almost instantly reversible by the simple addition of as little as 250 micrograms of Cr+3 per day over a 2 week period[x.]

Purposes and Advantages of Invention

An object of this invention is to disclose a long-term program effective in reversing the Chromium deficiency in Type II Diabetes victims, a Further objective is to reduce or even remove the need for daily insulin injections. Further objectives are to provide a method which allow diabetics to:
(1) retire for the evening with relatively low glucose numbers,
(2) restore more normal sleep patterns,
(3) reduce depression and carbohydrate craving,
(4) increase energy levels, muscle mass, workloads, weight loss, and overall sense of well being.

This invention provides diabetics with the ability to temporarily expedite a dramatic increase in the amount of serum glucose imported into the muscle cells. Because these cells are temporarily satiated with glucose, the glucagon signaling apparatus is interrupted, the liver suspends the release of glucose into the blood, and lower overnight glucose levels become much more obtainable.

Although the exercise regimen disclosed herein is intended as a part of a long-term program for restoring the body's depleted Chromium stores, it is also effective as a one-time treatment to mitigate the effects of a carbohydrate overdose. A Type III Diabetic who has ingested a dangerous amount of carbohydrates may rapidly and dramatically reduce his/her blood serum glucose levels by simply using the exercise regimen disclosed herein as soon after exposure to the excess carbohydrates as possible.

Preferred Embodiment

The invention consists of components which give Type II Diabetics the ability to effect dramatic, short-term reduction of blood sugar levels and to eventually replenish the body's stores of Chromium (III). The components are as follows:
a. A daily regimen of vitamins and tablets comprising
  i. Twice daily doses of a compound comprising the Chromium complex of an Organic Acid such as Picolinate, Nicotinate, Glycinate or other having a chromium content of between 100 and 500 micrograms of Chromium.
  ii. 200-1,000 milligram daily dose of a vaso-dilator/blood thinner comprising aspirin, niacin and L-Arginine.
  iii. doses of liquid Ionic chromium in the concentration of between 100-500 parts per million, such that each dose contains between 100 and 1,500 micrograms of chromium. Such compound is administered in a fashion which will introduce massive amounts of Cr(III) into the blood stream in a rapid manner, such as sublingually.
b. A complimentary exercise regimen comprising at least one daily aerobic exercise session of at least one-half hour each. The exercise should elevate and hold the heart rate at or above 60% of the maximum as established by the American Medical Association for the duration of the workout.
c. A method of administering the daily regimen:
  i. The Chromium Organic acid compound is ingested at least twice per day, usually in the morning and in the evening.
  ii. Approximately 10 minutes prior to each work out, The person ingests the vaso-dilator/blood thinner.
  iii. Immediately prior to workout, the person places the Ionic Chromium complex under the tongue (sublingual) and holds it there during the exercise for as long as possible before swallowing.
  iv. Approximately mid-way through the work out, the person repeats the sublingual administration of the Ionic Chromium complex.

Closest Known Prior Art

| Patent No. | Inventor | Date | Title |
| --- | --- | --- | --- |
| 4,571,391 | Riley, et al | Feb. 18, 1986 | Chromium acetylacetonate as a dietary supplement and pharmaceutical agent |
| 4,923,855 | Jensen | May 8, 1990 | Synthetic GTF chromium material and process therefor |

-continued

| Patent No. | Inventor | Date | Title |
|---|---|---|---|
| 4,954,492 | Jensen | Sep. 4, 1990 | Synthetic GTF chromium material for decreasing blood lipid levels and process therefor |
| 5,087,623 | Boynton, et al | Feb. 11, 1992 | Chromic picolinate treatment |
| 5,087,624 | Boynton, et al | Feb. 11, 1992 | Chromic picolinate treatment |
| 5,194,615 | Jensen | Mar. 16, 1993 | Synthetic GTF chromium nicotinate material and its preparation |
| 5,567,736 | Buchman, et al | Oct. 22, 1996 | Use of a choline salt to inhibit fatty liver in patients receiving total parenteral nutrition |
| 5,905,075 | Harpe, et al | May 18, 1999 | Chromium nicotinate compositions and uses thereof |
| 5,948,772 | de la Harpe, et al | Sep. 7, 1999 | Chromium picolinate compositions and uses thereof |
| 5,962,030 | Fine | Oct. 5, 1999 | Dietary supplement and method of treatment for diabetic control |
| 5,980,905 | de la Harpe, et al | Nov. 9, 1999 | Chromium polynicotinate compositions and uses thereof |
| 6,093,711 | de la Harpe, et al | Jul. 25, 2000 | Enteric-coated chromium picolinate compositions and uses thereof |
| 6,100,250 | de la Harpe, et al | Aug. 8, 2000 | Enteric-coated chromium polynicotinate compositions and uses thereof |
| 6,100,251 | de la Harpe, et al | Aug. 8, 2000 | Chromium polynicotinate compositions |
| 6,136,317 | de la Harpe, et al | Oct. 24, 2000 | Chromium picolinate compositions |
| 6,143,301 | de la Harpe, et al | Nov. 7, 2000 | Chromium picolinate compositions and uses thereof |
| 6,147,070 | Facchini | Nov. 14, 2000 | Methods and compositions for controlling iron stores to treat and cure disease states |
| 6,203,819 | Fine | Mar. 20, 2001 | Dietary supplement and method of treatment for diabetic control |
| 6,251,888 | de la Harpe, et al | Jun. 26, 2001 | Chromium picolinate compositions and uses thereof |
| 6,251,889 | de la Harpe, et al | Jun. 26, 2001 | Chromium picolinate compositions |
| 6,258,848 | Fantus | Jul. 10, 2001 | Methods and compositions for increasing insulin sensitivity |
| 6,323,192 | Harpe, et al | Nov. 27, 2001 | Chromium polynicotinate compositions and uses thereof for absorption of essential metals |
| 6,432,942 | de la Harpe, et al | Aug. 13, 2002 | Chromium picolinate compositions and uses thereof |
| 6,440,931 | Remmereit, et al | Aug. 27, 2002 | Conjugated linoleic acid in treatment and prophylaxis of diabetes |
| 6,471,998 | de la Harpe, et al | Oct. 29, 2002 | Chromium picolinate compositions |
| 6,541,005 | Yegorova | Apr. 1, 2003 | Compositions and methods for reducing or controlling blood cholesterol, lipoproteins, triglycerides and atherosclerosis |
| 6,544,525 | Yegorova | Apr. 8, 2003 | Compositions and methods for reducing or controlling blood cholesterol, lipoproteins, triglycerides and atherosclerosis |
| 6,548,687 | Yu, et al | Apr. 15, 2003 | Chromium L-threonate, process for preparation of the same and their use |
| 6,576,242 | Yegorova | Jun. 10, 2003 | Compositions and methods for reducing or controlling blood cholesterol, lipoproteins, triglycerides and atherosclerosis |
| 6,660,293 | Giordano, et al | Dec. 9, 2003 | Compositions and methods for prophylactic and therapeutic supplementation of nutrition in subjects |
| 6,689,383 | Anderson, et al | Feb. 10, 2004 | Chromium-histidine complexes as nutrient supplements |
| 6,713,469 | de la Harpe, et al | Mar. 30, 2004 | Chromium picolinate compositions and uses thereof |

| Patent No. | Inventor | Date | Title |
|---|---|---|---|
| 6,809,115 | Katz, et al | Oct. 26, 2004 | Methods and compositions for the treatment of diabetes, the reduction of body fat, improvement of insulin sensitivity, reduction of hyperglycemia, and reduction of hypercholesterolemia with chromium complexes, conjugated fatty acids, and/or conjugated fatty alcohols |
| 6,814,983 | Giordano, et al | Nov. 9, 2004 | Compositions and methods for nutrition supplementation |
| 6,818,229 | Cefali, et al | Nov. 16, 2004 | Intermediate release nicotinic acid compositions for treating hyperlipidemia |
| 6,818,233 | Perkes | Nov. 16, 2004 | Dietary supplements containing natural ingredients |
| 6,852,690 | Nauck, et al | Feb. 8, 2005 | Method and composition for enhanced parenteral nutrition |
| 6,852,760 | Fine, et al | Feb. 8, 2005 | Compositions and methods for treatment for glucose metabolism disorders |
| 6,863,904 | Giordano, et al | Mar. 8, 2005 | Compositions and methods for prophylactic and therapeutic supplementation of nutrition in subjects |
| 6,893,627 | Ribnicky, et al | May 17, 2005 | Method for treating type 2 diabetes with an extract of Artemisia |
| 6,893,656 | Blitzer, et al | May 17, 2005 | Athletic patch |
| 6,955,883 | Margus, et al | Oct. 18, 2005 | Life sciences business systems and methods |
| 6,967,030 | Wright, et al | Nov. 22, 2005 | Formulation for insulin and glucose control |
| 6,967,204 | Fryburg, et al | Nov. 22, 2005 | Treatment of insulin resistance syndrome and type 2 diabetes with PDE9 inhibitors |
| 6,995,166 | Giordano, et al | Feb. 7, 2006 | Method and composition for supplementation of nutritional deficiencies in renal patients |

[i] Sargent T, Lim TH, Jenson, RL: "Reduced Chromium Retention in Patients with Hemochromatosis, a Possible Basis of Hemochromatotic Diabetes" Metabolism: 1979: 28:1, p 70-79
[ii] Maher, Timothy J. Chromium and Other Minerals in Diabetes Mellitus, U.S. Pharmacist, 2000: 24:11
[iii] Vincent, J., "Biochemistry of Chromium, J. Nutrition 2000; 130: 715-718
[iv] Vincent, ibid
[v] Brock, J. H., "Transferrins." Harrison P. (ed) Metalloproteins 1985: vol.2: 183-262 MacMillan, London
[vi] Lim, T, Sargent, T., Kusubov, N. "Kinetics of Trace Element Chromium (III) in the Human Body" Am J. Physiology, 1983: 244(4): R445-54
[vii] Davies, S., et al, "Age-related decreases in chromium levels in 51,665 hair, sweat, and serum samples from 20,872 patients - implications for the prevention of cardiovascular disease and Type II diabetes mellitus", Metabolism, 1997; 46(5) 469-73
[viii] Jiang, G., Zhang, B. "Glucagon and Regulation of Glucose Metabolism" Am J Phsiol Endocrinol Metab. 2003 284: E671-8
[ix] Davies, ibid
[x] Jeejeehboy, K., et al, "Chromium Deficiency, Glucose Intolerance and Neuropathy reversed by Chromium Supplementation in a Patient Receiving Long-Term Parenteral Nutrition:" Am J. Clin Nutr. 1977; 30*pp. 531-8

I claim:

1. A method for reducing blood serum glucose in a patient, comprising:
   (a) administering vasodilator to the patient in amounts effective to increase blood flow in tissues; and subsequently
   (b) administering ionic chromium to the patient in amounts effective to reduce the levels of blood serum glucose and to stabilize the blood serum glucoses levels.

2. The method according to claim 1 wherein the vasodilator is administered at a rare of from 200 milligram to 1,000 milligram per day.

3. The method according to claim 1 wherein the vasodilator comprises a mixture of aspirin, niacin, and L-arginine or L-citruline.

4. The method according to claim 1 wherein the ionic chromium is administered at a rate of from 100 to 1,500 micrograms twice a day.

5. The method according to claim 1 wherein the ionic chromium is a chromium complex.

6. The method according to claim 5 wherein the chromium complex comprises dissolved chromium salt of halide.

7. The method according to claim 5 wherein the chromium complex further comprises organic acid.

8. The method according to claim 7 wherein the organic acid is selected from a group consisting of amino acid, picolinate, nicotinate, ascorbate, oxalate, glycinate, and any combination thereof.

9. The method according to claim 1 wherein the ionic chromium is administered orally, nasally, sublingually, intramuscularly, subcultaneously, and transdermally.

* * * * *